US007936908B2

(12) United States Patent
Brackett

(10) Patent No.: US 7,936,908 B2
(45) Date of Patent: May 3, 2011

(54) GRAPHICAL USER INTERFACE FOR DISPLAYING A RADIOLOGY IMAGE FOR A PATIENT AND AN ASSOCIATED LABORATORY REPORT SUMMARY

(75) Inventor: C. Cameron Brackett, Overland Park, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 1089 days.

(21) Appl. No.: 11/684,235

(22) Filed: Mar. 9, 2007

(65) Prior Publication Data

US 2008/0219524 A1 Sep. 11, 2008

(51) Int. Cl.
G06K 9/00 (2006.01)
G06F 3/00 (2006.01)

(52) U.S. Cl. ......... 382/128; 382/130; 382/131; 715/700
(58) Field of Classification Search .................. 382/128, 382/130, 131, 132; 715/700
See application file for complete search history.

(56) References Cited

U.S. PATENT DOCUMENTS

| | | | |
|---|---|---|---|
| 4,828,716 A | 5/1989 | McEwen | |
| 5,924,074 A | 7/1999 | Evans | |
| 6,367,104 B1 | 4/2002 | Falbo et al. | |
| 6,574,742 B1 | 6/2003 | Jamroga | |
| 6,678,703 B2 | 1/2004 | Rothschild | |
| 6,684,092 B2 | 1/2004 | Zavislan | |
| 7,072,501 B2* | 7/2006 | Wood et al. | 382/132 |
| 7,120,644 B1 | 10/2006 | Canessa et al. | |
| 7,260,480 B1 | 8/2007 | Brown | |
| 7,302,164 B2 | 11/2007 | Wright | |
| 7,353,114 B1 | 4/2008 | Rohlf et al. | |
| 7,693,317 B2* | 4/2010 | Vining et al. | 382/128 |
| 2002/0038226 A1 | 3/2002 | Tyus | |
| 2002/0077864 A1 | 6/2002 | Cavallaro et al. | |
| 2002/0156650 A1* | 10/2002 | Klein et al. | 705/2 |
| 2003/0120458 A1 | 6/2003 | Rao et al. | |
| 2004/0167800 A1 | 8/2004 | Chang et al. | |
| 2004/0172292 A1* | 9/2004 | Takekoshi et al. | 705/2 |
| 2004/0225531 A1 | 11/2004 | Serrano et al. | |
| 2005/0213832 A1 | 9/2005 | Schofield et al. | |
| 2006/0010013 A1* | 1/2006 | Yamatake | 705/2 |
| 2006/0242143 A1* | 10/2006 | Esham et al. | 707/6 |
| 2007/0130165 A1* | 6/2007 | Sjoblom et al. | 707/10 |
| 2007/0167754 A1 | 7/2007 | Okuno | |

OTHER PUBLICATIONS

Non-final Office Action dated Apr. 28, 2010 in U.S. Appl. No. 11/684,228.
Non-final Office Action dated Jun. 2, 2010 in U.S. Appl. No. 11/684,220.
Non-Final Office Action mailed Dec. 14, 2010 in U.S. Appl. No. 11/684,220.

* cited by examiner

Primary Examiner — John B Strege
(74) Attorney, Agent, or Firm — Shook, Hardy & Bacon L.L.P.

(57) ABSTRACT

A user interface embodied on at least one computer readable medium for displaying a healthcare image for a patient and a clinical report for a patient simultaneously is provided. The interface comprises a first display area configured to display a healthcare image for a patient and a second display area configured to display a clinical report associated with the healthcare image simultaneously with the healthcare image for the patient, where the clinical report is created based on results other than the healthcare image.

21 Claims, 8 Drawing Sheets

GRAPHICAL USER INTERFACE FOR DISPLAYING A RADIOLOGY IMAGE FOR A PATIENT AND AN ASSOCIATED LABORATORY REPORT SUMMARY

CROSS-REFERENCE TO RELATED APPLICATIONS

This application is related to commonly assigned U.S. application Ser. No. 11/684,220 entitled "SYSTEM AND METHOD FOR ASSOCIATING ELECTRONIC IMAGES IN THE HEALTHCARE ENVIRONMENT", filed Mar. 9, 2007, and U.S. application Ser. No. 11/684,228 entitled "SYSTEM AND METHOD FOR ASSOCIATING A PATIENT SPECIMEN IDENTIFIER WITH A RADIOLOGY IMAGE FOR THE PATIENT", filed Mar. 9, 2007, the disclosures of which are hereby incorporated by reference herein.

STATEMENT REGARDING FEDERALLY SPONSORED RESEARCH OR DEVELOPMENT

Not Applicable.

BACKGROUND

Oftentimes in a healthcare environment, it is necessary to capture images of a patient. These images can include radiology images, laboratory images, pictures, cardiology images and a variety of other images. These images can be captured electronically in a variety of ways and are used for treatment of the patient. Patient information, such as reports for the images, may also be entered and recorded in a health (or clinical) information system.

While patient information is stored in a clinical information system, the captured images are stored in an archive. Picture archiving and communication systems (PACS) are exemplary digital archives for storing healthcare images. The captured healthcare images may be stored in a variety of formats including DICOM (Digital Imaging and Communications in Medicine) and non-DICOM formats.

DICOM images are archived according to specific standards for storing, transmitting and handling information in medical imaging. The standards include file format definition and network communications protocol. DICOM groups images together with information such as patient identification so each image is not mistakenly separated from the patient identification. Non-DICOM healthcare images do not adhere to the specific DICOM standards.

Currently, PACS digital archives can store both DICOM and non-DICOM images. However, the image viewers to view DICOM and non-DICOM viewers are separate. Current PACS do not have the ability to relate DICOM and non-DICOM images for a patient since the proper patient record context to support association of the images is lacking.

SUMMARY

In one embodiment, a method for displaying a healthcare image for a patient and a clinical report for the patient simultaneously is provided. The method comprises displaying a healthcare image for a patient and displaying at least one graphical indicia indicating a region of the healthcare image. The method further comprises receiving selection of one of the at least one graphical indicia and in response to the selection of the one of the at least one graphical indicia, determining a clinical report associated with the region of the healthcare image, where the clinical report does not contain an interpretation of the healthcare image for the patient. The method further comprises simultaneously displaying the clinical report associated with the region of the healthcare image with the display of the healthcare image for the patient.

In yet another embodiment, a user interface embodied on at least one computer readable medium for displaying a healthcare image for a patient and a clinical report for a patient simultaneously is provided. The interface comprises a first display area configured to display a healthcare image for a patient and a second display area configured to display a clinical report associated with the healthcare image simultaneously with the healthcare image for the patient, wherein the clinical report is created based on results other than the healthcare image.

In still another embodiment, a user interface embodied on at least one computer readable medium for displaying a radiology image for a patient and an associated laboratory image for the patient is provided. The user interface comprises a first display area configured to display a radiology image for a patient and a second display area configured to display one or more graphical indicia each indicating a region of the radiology image. the interface further comprises a third display area configured to display a laboratory report associated with a selected region of the radiology image and a fourth display area configured to display a laboratory image associated with the laboratory report.

In yet another embodiment, a user interface embodied on at least one computer readable medium for displaying a radiology image and a laboratory image for a patient is provided. The user interface comprises a first display area configured to display a radiology image for a patient and a second display area configured to display at least one laboratory image for the patient, the at least one laboratory image being associated with the radiology image.

BRIEF DESCRIPTION OF THE SEVERAL VIEWS OF THE DRAWINGS

The present invention is described in detail below with reference to the attached drawing figures, wherein.

DETAILED DESCRIPTION

Embodiments of the present invention are directed to systems and methods for capturing and documenting images in the healthcare environment. The systems and methods of the present invention not only have the ability to store DICOM and non-DICOM images from various modalities and departments within a healthcare facility, but display the images in the context related to other procedures.

The system and method allow for this association of two separate and distinct medical images for a patient with proper context. The ability to associate a defined region of one image to a second image from another study is also provided. Separate and distinct image sets may be associated by receiving a defined region of a given image to associate with a second image.

Having briefly described an overview of the present invention, embodiments of the invention will be discussed with reference to FIGS. 1-7.

Figure 1:
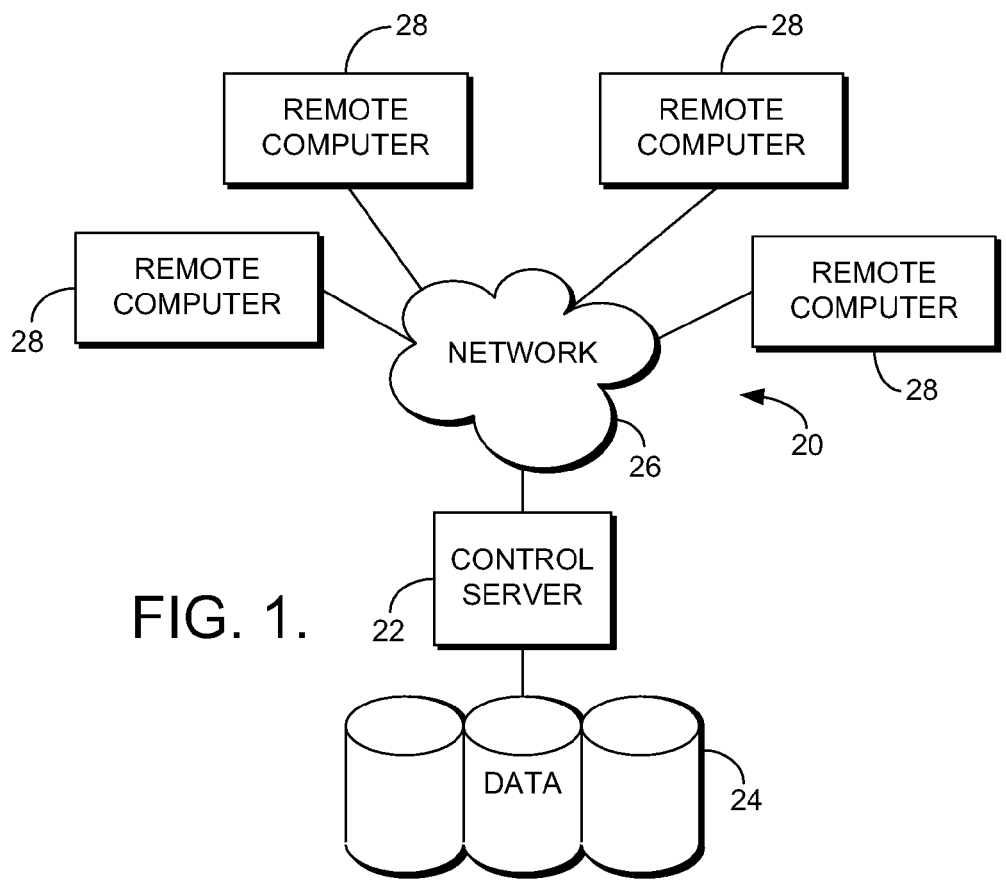
FIG. 1 is a block diagram illustrating components of a system for use in accordance with an embodiment of the present invention.

With reference to FIG. 1, an exemplary medical information system for implementing embodiments of the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, discharge planners, care planners, physician's assistants, nurse practitioners, nurses, nurse's aides, pharmacists, dieticians, microbiologists, laboratory experts, laboratory scientist, laboratory technologists, genetic counselors, researchers, veterinarians and the like.

The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet.

In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention. Although the method and system are described as being implemented in a LAN operating system, one skilled in the art would recognize that the method and system can be implemented in any system.

Figure 2:
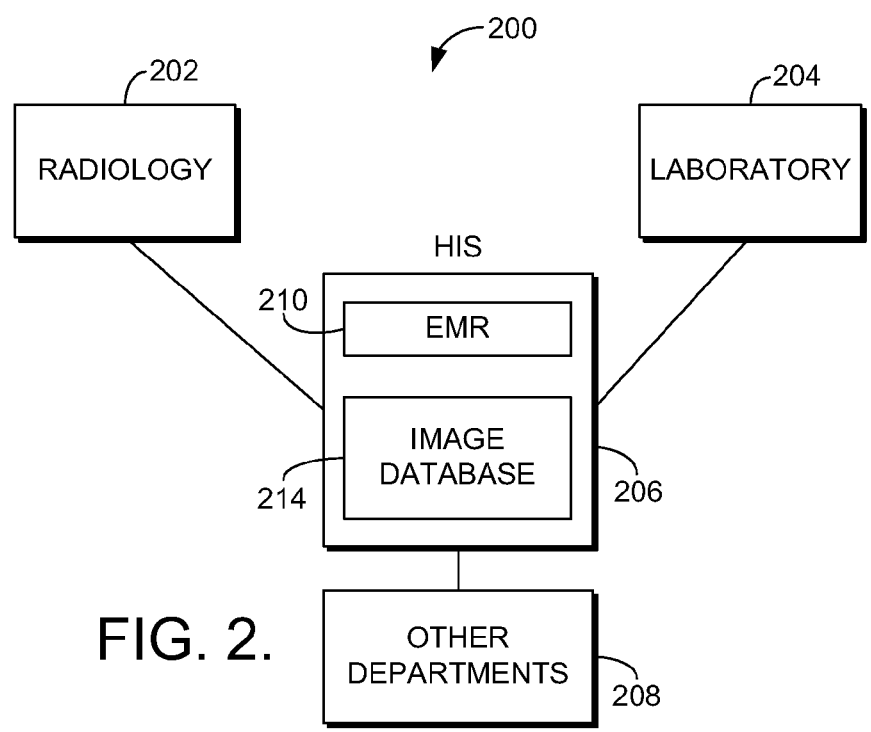
FIG. 2 is a block diagram illustrating components for a system for capturing and documenting images in a healthcare environment in accordance with an embodiment of the present invention.

With reference to FIG. 2, a block diagram is provided illustrating an exemplary architecture for facilitating the association of images in a healthcare environment in accordance with an embodiment of the present invention. As shown in FIG. 2, a health information system (HIS) 206 may be provided to manage patient records 210 and an image database 214. The patient records may be in the form of electronic medical records. The image database 214 stores and maintains DICOM and non-DICOM images in computerized database. Exemplary DICOM and non-DICOM images include radiology images, laboratory images, pictures, cardiology images, such as ECHO images, and other medical images. One of skill in the art will appreciate that the database may be maintained separately or may be integrated.

As shown in FIG. 2, the HIS 206 is capable of communicating with a number of departments and applications, such as the radiology department 206, the laboratory department 204 and other departments 208 within the healthcare facility. Images and related reports are sent from the radiology department 202 via a radiology application to the HIS 206. Images and related information are also sent from the laboratory department 204 via a laboratory application to the HIS 206. Other departments within a healthcare facility 208 may also send DICOM and non-DICOM images and related reports to be stored and maintained in the HIS 206.

It should be noted that the departments communicating with the HIS 206 in FIG. 2 are provided by way of example only and are not intended to limit the scope of the present invention. Each department may have a computing device, such as a remote computer 28 of FIG. 1, for communicating with the HIS 206 of FIG. 2. In addition, communication between the HIS 206 and the various departments may be via one or more networks, which may comprise one or more wide area networks (WANs) and one or more local area networks (LANs) as well has one or more public networks, such as the Internet, and one or more private networks. In embodiments, the EMR, radiology application, laboratory application and other applications may be part of a common unified clinical system in which common services are employed for functions common to the various applications. One example is the CERNER MILLENNIUM clinical computing system, such as CERNER MILLENNIUM.

In operation, by way of example and not by limitation, at least one DICOM image of a patient, such as a radiology image, is taken. In one embodiment, the radiology department captures the radiology image of the patient. The DICOM image is analyzed and a report summarizing the findings of the radiology department 202 is associated with the image. The DICOM image is communicated to and maintained in the image database 214 and the report is maintained in the patient records of EMR 210 of the HIS 206.

Based on the radiology department's findings, additional testing of the patient may be needed. For instance, if a mass is found in the DICOM radiology image, the additional testing for the patient may be to have a biopsy of the mass completed and tested. The patient has the biopsy performed and a clinician, such as a pathologist, interprets the results of the biopsy and enters the results in a laboratory report. The laboratory report analyzing the findings of the laboratory department 204 is communicated to and maintained in the patient records 210 of the HIS 206. One or more non-DICOM images of the laboratory test results of the biopsy may be associated with the report and may be communicated and maintained in the image database 214.

In another embodiment, one department captures a first image for the patient. The first image may be a DICOM or non-DICOM image. The first image is communicated to and maintained in the image database 214 and any associated report or information for the image is maintained in the patient records 210 of the HIS 206. In embodiments, a different department captures a second image for the same patient. For example, the first department may be the cardiology department and the second department may be the radiology department. The second image is related to the first image and may be a DICOM or non-DICOM image. The second image is communicated and maintained in the image database 214. Associated reports for the second image along with association with the first image are maintained in patient records 210 of the HIS 206.

Figure 3A:
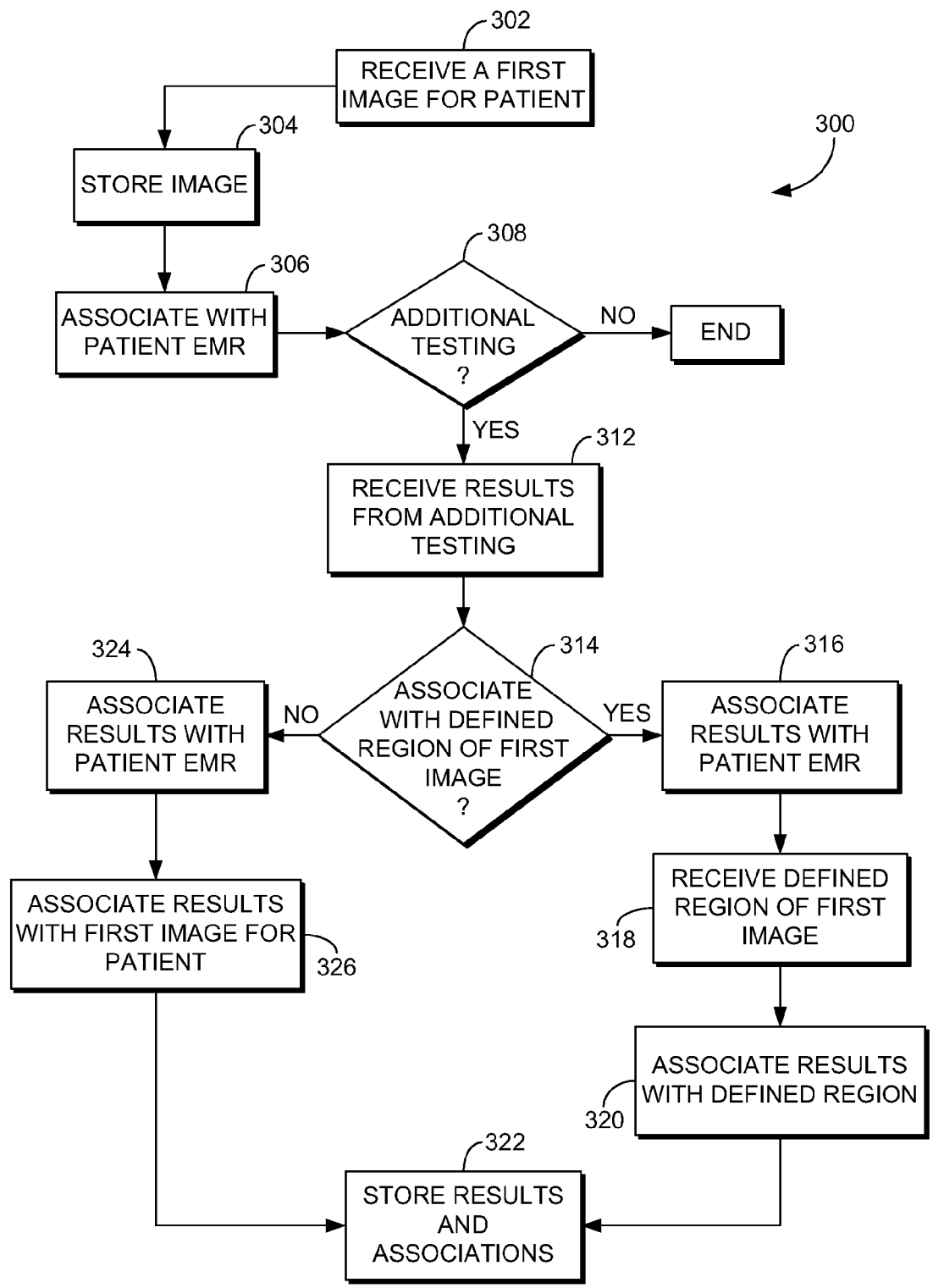
FIG. 3A is a flow diagram illustrating a method for storing and associating multiple images in accordance with an embodiment of the present invention.

With reference to FIG. 3A, a method for storing and associating images in a healthcare environment is shown. At step 302, a first image for a patient is received. For example, the patient may have had a DICOM radiology image created. This image at step 304 is communicated to and stored in a computerized database such as image database 214. The related report entered by a clinician, such as a radiologist, for the image and is communicated to and stored in a computerized database such as the patient records 210 of FIG. 2. At step 306, the image received is associated with the patient's electronic medical record. This may be done by adding a link or reference to the image in the patient's records.

At step 308, it is determined whether any additional testing is needed for the patient based on the findings for the first image received. The first image may be a DICOM or non-DICOM image. For example, if a mass is found in the DICOM radiology image, additional laboratory testing may be ordered by the clinician. If additional testing is needed for the patient the system proceeds to step 312. At step 312, the results from the additional testing for the patient are received. For example, laboratory test results, in the form a laboratory report, for a biopsy of the mass on the DICOM radiology image may be received. In one embodiment, non-DICOM images, such as digital pictures of the laboratory slides, may accompany the laboratory report. For example, a non-DICOM laboratory image may be created and then communicated to the system for a biopsy of the mass detected by the DICOM radiology image.

At step 314, it is determined whether the results should be associated with a defined region of the first image. If the results for the patient are not to be associated with a defined region of the first image, then at step 324 the results are associated with the patient's electronic medical record. At step 326, the results are associated with the first image for the patient. At step 322, the results and associations are communicated and maintained in computerized databases.

If at step 314 it is determined that the results are to be associated with a defined region of the first image, at step 316, the results (i.e., a laboratory report) are associated with the patient's electronic medical record. At step 318, an identification (or definition) of the portion of the first image with which the results are to be associated is received. For example, the portions may be defined by regions and/or coordinates. The defined region (or coordinates) is used to associate the relevant part of the first image with the results of the additional testing at step 320. One of skill in the art will appreciate that a variety of techniques may be used to associate the results with a region, location or coordinates of a radiology image. For example, a clinician (i.e., a pathologist) may highlight the location of the region on a computer display to identify the relevant portion and then manually entering the accession number of the specimen taken from the region. Alternatively, from the laboratory report, a clinician may enter coordinates of the region or an identifier of the region of the image to associate the laboratory report to the image. Once the association is made at step 320, the results and associations are communicated and stored at step 322. In embodiments, the results and associated are stored in a computerized database such the HIS 206 of FIG. 2.

Figure 5:
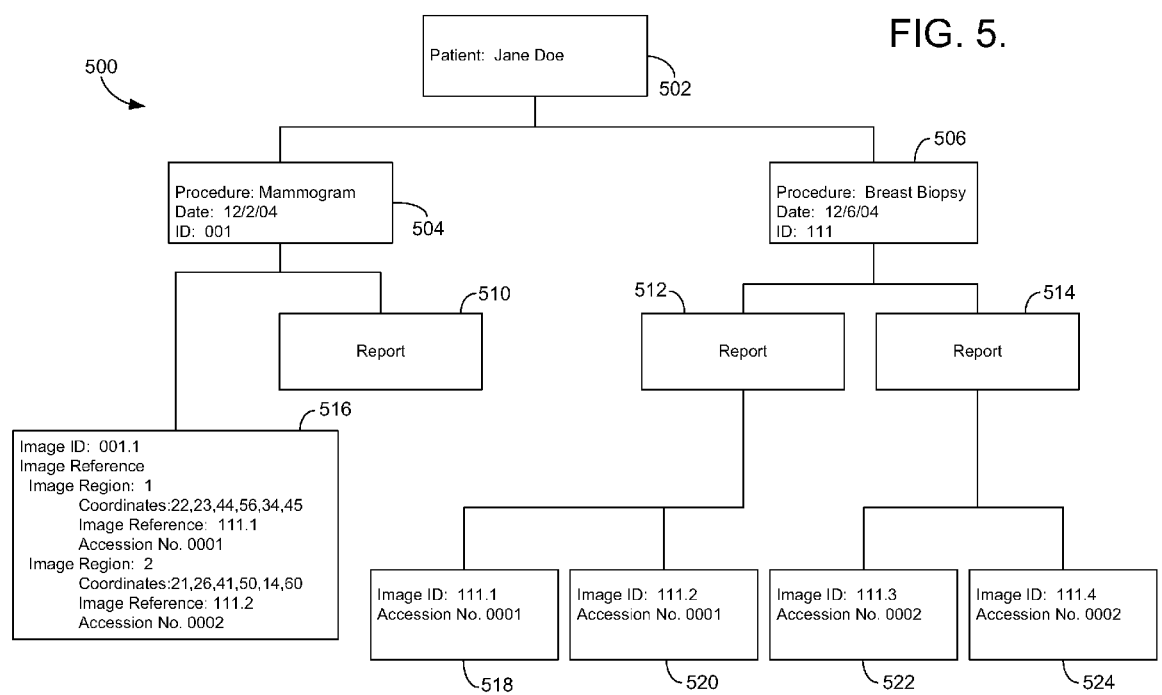
FIG. 5 is block diagram illustrating association of multiple images for a patient in accordance with an embodiment of the present invention.

For example, with reference to FIG. 5, an exemplary data structure 500 is shown for associating test results for two biopsies to defined two separate regions of a radiology image 516 associated with the location of the masses from which the biopsies were taken. Specifically, the radiology image 516 and associated report 504 have been stored for a mammography procedure 504 performed for patient Jane Doe 502. In this example, biopsies of two masses were ordered for Jane Doe 502 in response to an interpretation by a radiologist of the radiology image 516.

In response, a clinician, such as a surgeon or pathologist, performed a biopsy procedure 506 for the patient. At or before the time of the biopsy, the specimen for each mass is assigned an accession number. For example, the specimen of the first mass is assigned an accession number of 0001 and the specimen of the second mass is assigned an accession number of 0002. The accession number of the specimen may be entered in a variety of ways such as into electronic user documentation or by scanning a bar code on a specimen collection container.

Each specimen is prepared for review by a pathologist. For example, for the biopsy of the first mass assigned accession number 0001, two slides 518 and 520 may be prepared for the pathologist's review and digital images may be made. The pathologist reviews slides 518 and 520 and/or the digital images of the slides, and prepares a report summarizing the results. For example, based on slides 518 and 520, the pathologist prepares a report 512 that the first mass indicates stratified nevus cells indicative of a class IV malignancy and the speculated visibility suggests alternative locations. At this point, the clinician may designate a region on the radiology image 561 and associate the report for the biopsy of the first mass to the region. The clinician may designate a region on the radiology image by entering coordinates or by indicating or highlighting the location of the region on the image. In other embodiment, the regions may have been previously designated by another user, such as a radiologist.

The pathologist may associate report 512 for the specimen having accession number 0001 with the image region 1 of the radiology image 0001.1. For the second specimen, the pathologist may associate report 514 (and associated slides 522 and 524) for the specimen having accession number 0002 with the image region 2 of the radiology image 0001.1.

Figure 3B:
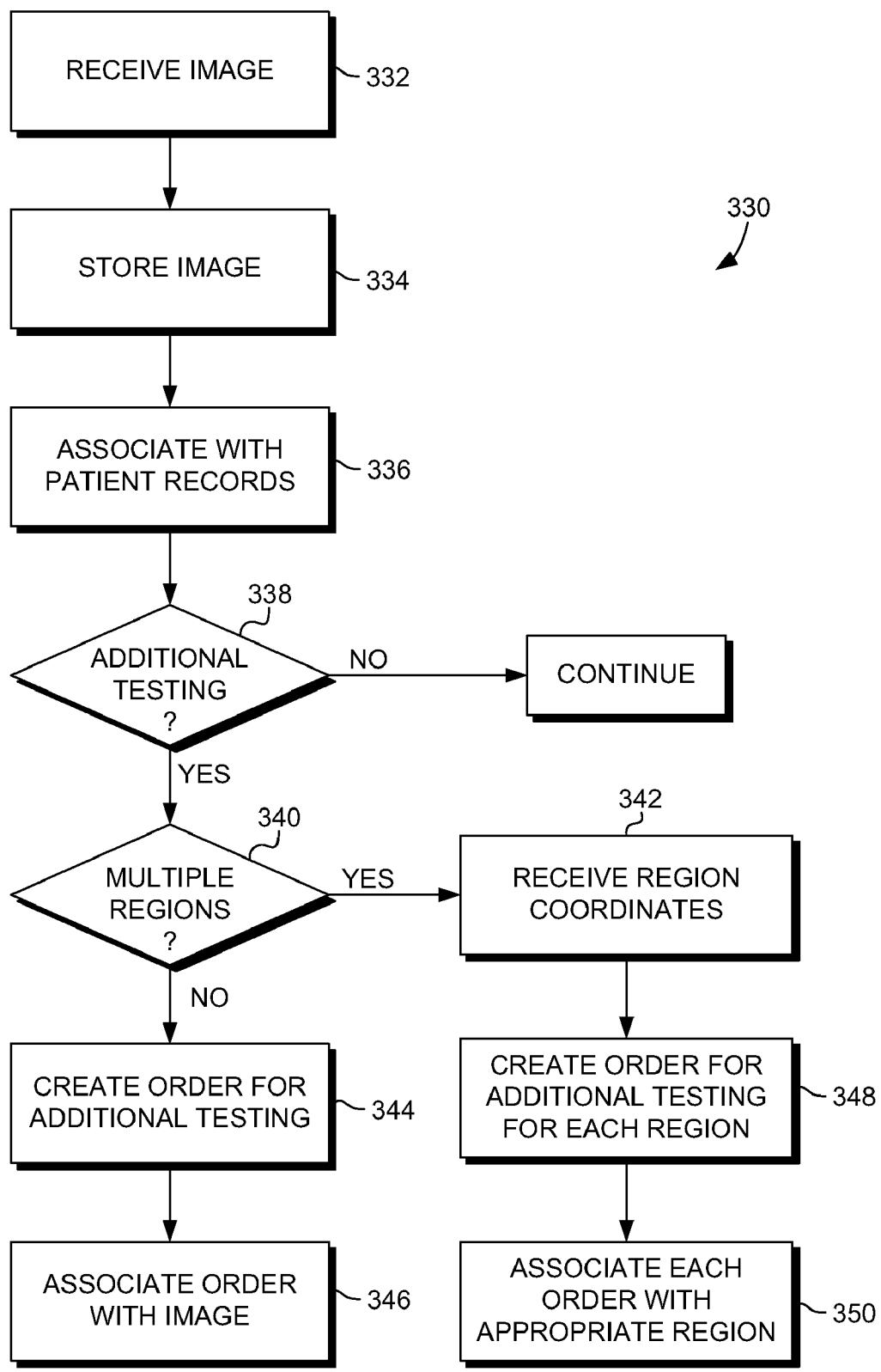
FIG. 3B is a flow diagram illustrating a method for creating orders for additional healthcare testing in accordance with an embodiment of the present invention.

With reference to FIG. 3B, a method 330 is provided for creating an order for additional testing based off a read or interpretation of a DICOM image. Initially, at step 332, a first image, such as a radiology DICOM image, is received for a patient. At step 334, the image is stored in an image database, such as image database 214 of HIS 206 (FIG. 2). At step 336, the first image is associated with patient records. For instance, the image may be referenced or linked to an electronic medical record for the patient. At step 338, it is determined if any additional testing should be done for the patient. For example, a clinician may provide an order for a biopsy based on the identification of a mass in the radiology image. If it is determined that no additional testing is needed at step 338, then no order is entered and the care process continues outside of this method. If at step 338 it is determined that additional testing should be completed, at step 340, it is determined whether there are multiple regions of the body as shown in the first image that should be tested. For example, if a clinician, such as a radiologist, views two masses in the radiology image, the clinician designates two regions on the image for testing. For example, the clinician may designate coordinates for one region for a first mass and coordinates for a second region for a second mass to be tested. At step 344, an order for additional testing to be done for the patient, such as a biopsy on one or more masses, is created. In this instance, orders for biopsies of each region would be created.

At step 340, if it is determined that there is only one region, at step 344, an order for additional testing is created. For example, if the first image is interpreted by a clinician as only have one mass, an order for a biopsy of the one mass is created. At step 346, the order created for the additional testing is associated with the first image. For example, the order may include the image identification number of the first image. Although, it will be appreciated that the order and the first image may be associated in a variety of ways.

Figure 3C:
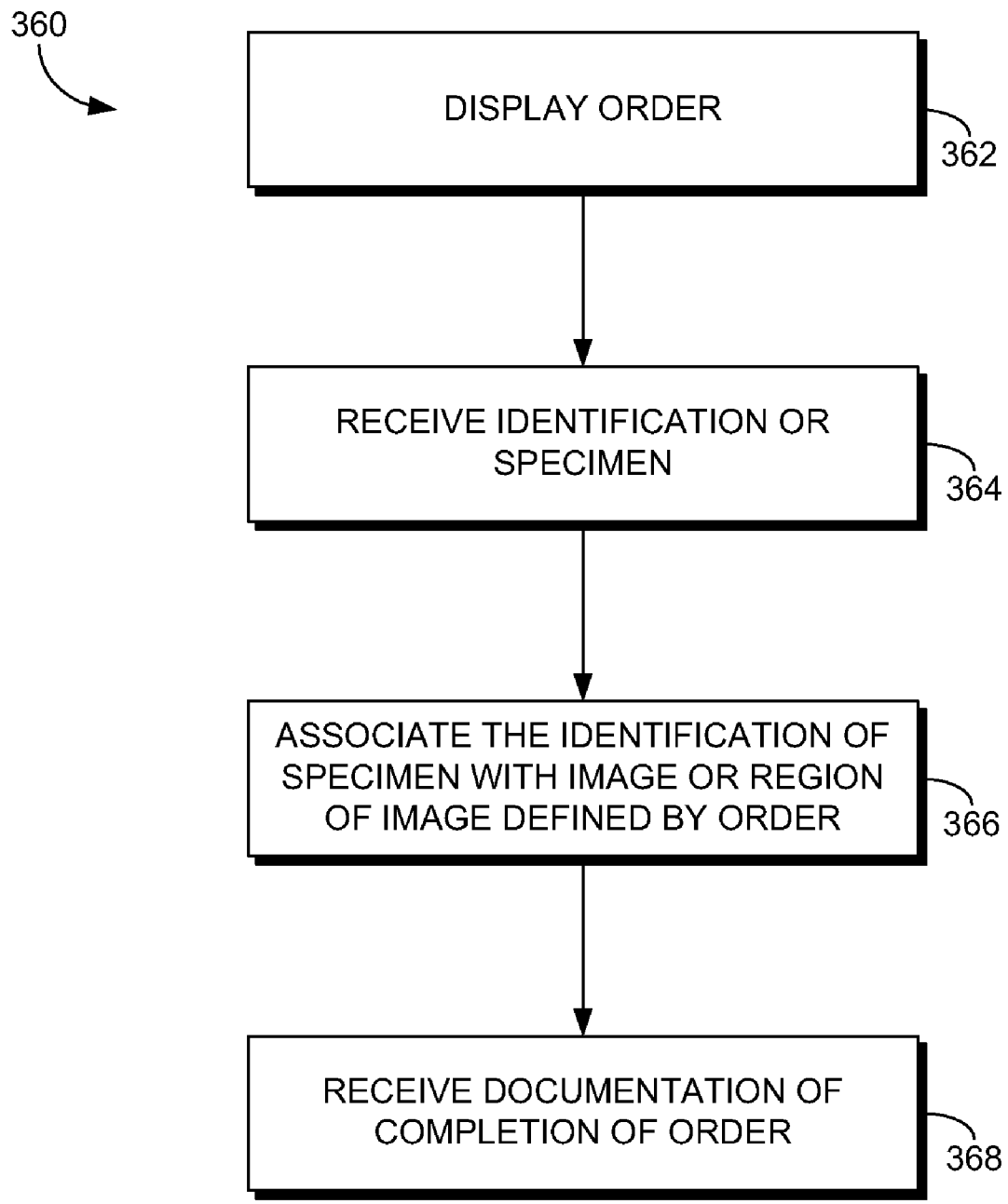
FIG. 3C is a flow diagram illustrating a method for associating a specimen identifier with a radiology image in accordance with an embodiment of the present invention.

With reference to FIG. 3C, a method 360 is provided for associating a specimen identifier with an image. At step 362, an order for a patient is displayed. For example, the order may be displayed to a clinician, such as a surgeon or pathologist, performing the additional testing on the patient. For example, the clinician may perform a biopsy on the patient. At step 364, identification of the specimen collected for the biopsy is received. For example, the identification of the specimen may be an identifier such as an accession number. The accession number of the sample may be entered in a variety of ways such as by a user documenting the order or scanning a bar code on a specimen collection container. At step 366, the identification of the specimen, such as an accession number, is associated with the image defined by the order. Thus, if the order is linked to the first image, as described above with reference to FIG. 3B, the accession number of the specimen collected is associated with the first image. For example, with reference to FIG. 5, the accession number of the specimen collected and the image identification may be maintained in a database or table. If the order is linked to more than one region, the accession number of the specimen collected from the region identified in the image is associated with the appropriate region. For example, with reference to FIG. 5, accession number 0001 for a specimen collected for the first mass defined by region 1 is associated with region 1 and accession number 0002 for the specimen collected for the second mass defined by region 2 is associated with region 2. Thus, any report for the specimen accession number and any associated pathology images are now linked by accession number to the appropriate region of the radiology image for the patient. At step 368, documentation of the completion of the order is received.

Figure 4:
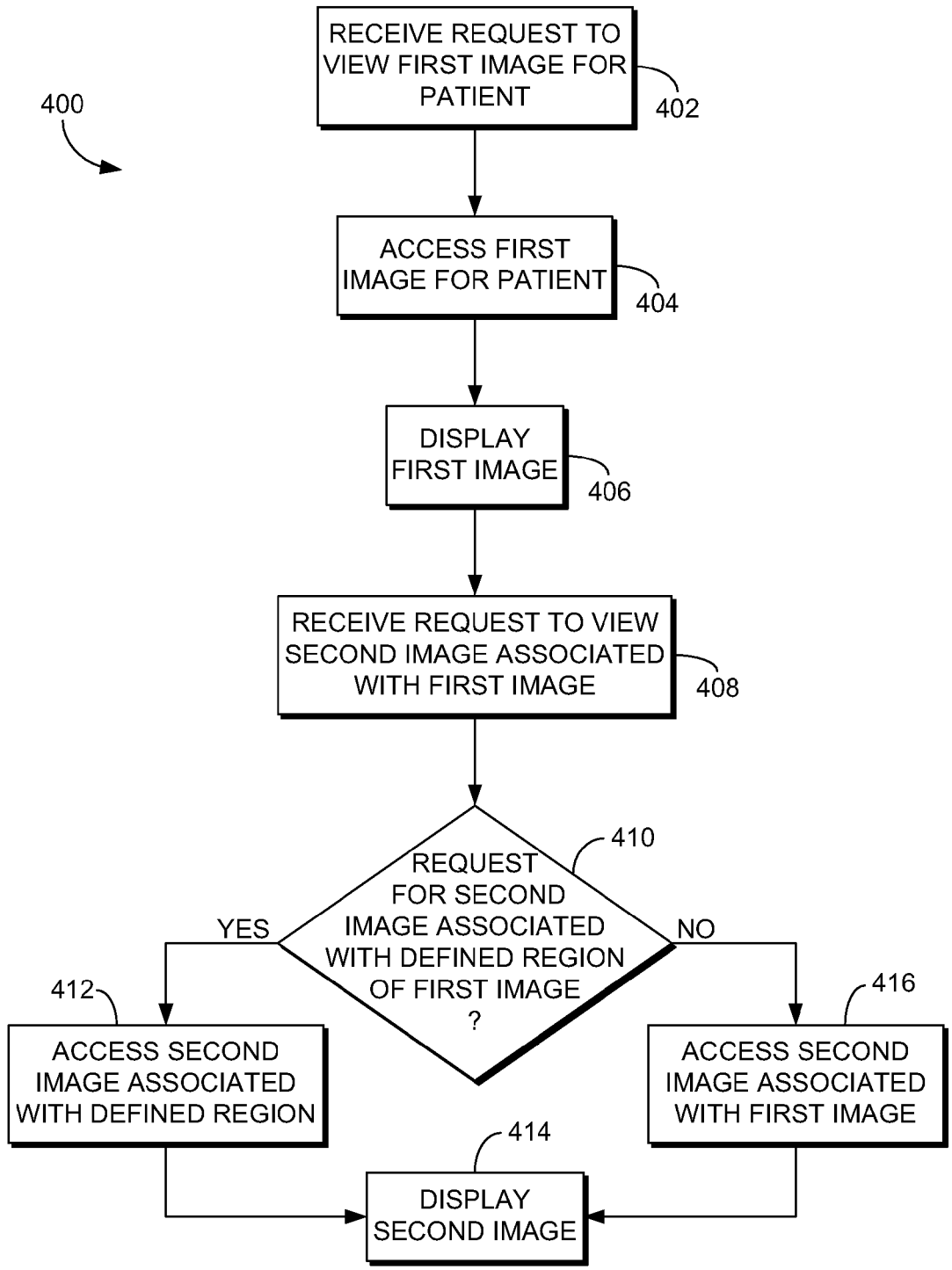
FIG. 4 is a flow diagram illustrating a method for displaying associated images in accordance with an embodiment of the present invention.

With reference to FIG. 4, a method 400 for displaying a first and second image for a patient in accordance with an embodiment of the present invention is shown. At step 402, a request to view a first image for a patient is received. For example, a healthcare provider may request to view a stored image for a patient. At step 404, the requested first image for the patient, associated report and patient data is accessed from the HIS. At step 406, the first image is displayed on a display screen, viewer, CPU or electronic media in accordance with an embodiment of the present invention. At step 408, while the first image is being displayed, a request to view a second image associated with the first image is received.

At step 410, it is determined whether the request for the second image is for a defined region of the first image. If it is determined at step 410 that the request for the second image is not associated with a defined region of the first image, at step 416, one or more second images associated with the first image are accessed and are displayed at step 414. If at step 410 it is determined that the second image is associated with a defined region of the first image, at step 412, the second image associated with the requested defined region of the first image is accessed and the appropriate second image is displayed at step 414 in a manner associating the second image with the appropriate region of the first image.

Figure 6:
FIG. 6 is an exemplary screen displaying a DICOM image in accordance with an embodiment of the present invention.

With reference to FIG. 6 an exemplary screen 600 of a radiology image for a patient is shown. In this instance, the radiology image is a mammography image for a patient. By way of example only, and not by limitation from image 600, a user may select to view one or more associated images by selecting related images 604 icon. This will access and present reports and images for the patient related to image 600. For example, a summary of a pathology report and images created for a biopsy of a mass found in the mammography radiology images may be presented. These images may be DICOM or non-DICOM images.

Alternatively, the user may select a portion (where the portion is a defined region rendered as graphical indicia) 602 of the image 600 and the one or more images associated with the selected portion selected can be shown. For example, a user may select region 602 on the radiology image 600 where a mass is indicated. Selection of region 602 will access and present a pathology report summary and images related to region 602. For example, one or more pathology images created for a biopsy from the selected region and a related report summary are displayed.

Figure 7:
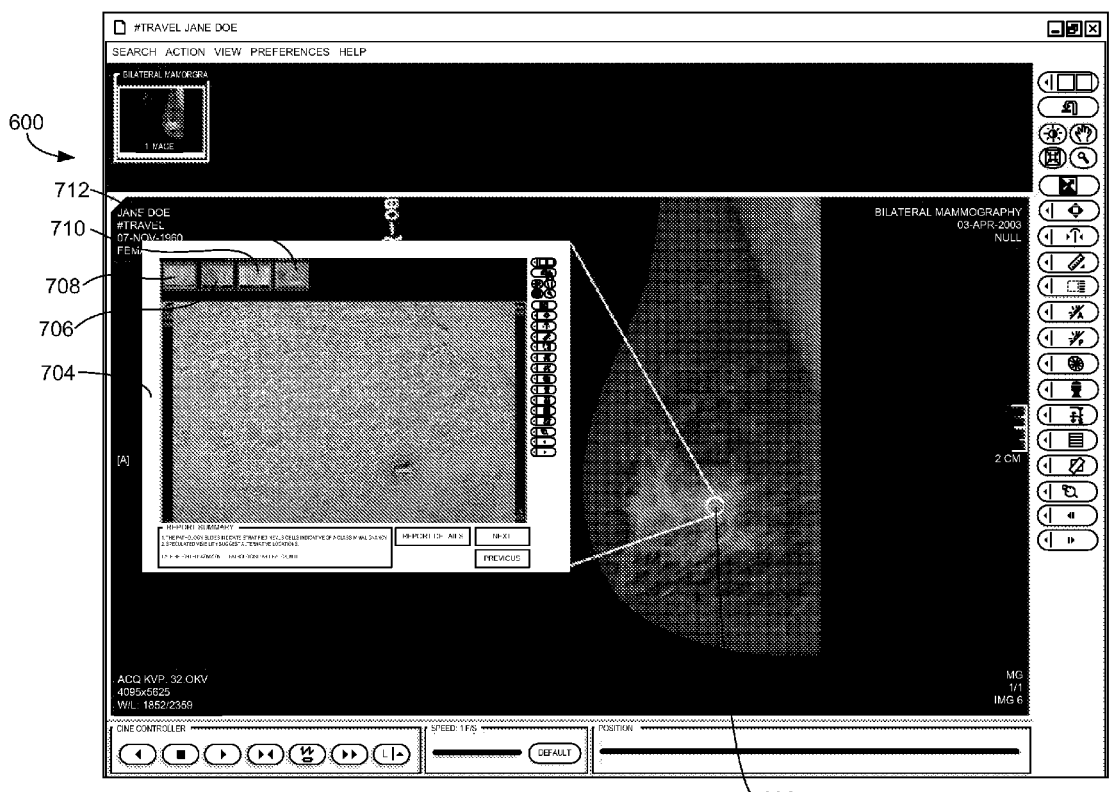
FIG. 7 is an exemplary screen displaying a DICOM image and a non-DICOM image in accordance with an embodiment of the present invention.

With reference to FIG. 7, a display of the radiology image 600 for the patient, and the associated report summary and related laboratory images related to the selected image are shown. Thumbnail images 706, 708, 710 and 712 associated with selected region 602 are displayed. Thumbnail images 706, 708, 710 and 712 are the laboratory images related to the selected region 602 of the radiology image 600. Any one of the thumbnail images may be selected for a larger image. For example, thumbnail image 708 is enlarged as full image 704. Any, some or all of the associated laboratory images 706, 708, 710 and 712 may be displayed simultaneously with the radiology image 600. Also displayed is a report summary. The report summary for the selected region 602 indicates that the pathology slides indicated stratified nevus cells indicative of a class IV malignancy and speculated visibility suggests alternative locations. A user may select "report details" to obtain the full pathology report related to the selected region. The display provides an interface that allows a clinician to view radiology images, related pathology reports and related pathology images in one view. The display further provides the clinician the ability to easily access additional pathology report details from the radiology image screen.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. A method for displaying a healthcare image for a patient and a clinical report for the patient simultaneously, the method comprising:

displaying on an interface a healthcare image for a patient;

receiving selection from the interface of at least one graphical indicia indicating a defined region of the healthcare image, wherein the defined region is a portion of the healthcare image;

in response to the selection of the one of the at least one graphical indicia, determining a clinical report associated with the defined region of the healthcare image, where the clinical report does not contain an interpretation of the healthcare image for the patient; and simultaneously displaying the clinical report associated with the defined region of the healthcare image with the display of the healthcare image for the patient.

2. The method of claim 1, wherein the graphical indicia is selected by a user hovering over or clicking on the graphical indicia.

3. The method of claim 2, wherein a different clinical report is associated with each region of the healthcare image.

4. The method of claim 1, further comprising:

accessing a data store to determine the clinical report for the patient associated with the region of the radiology image requested.

5. The method of claim 1, wherein the clinical report is a laboratory report.

6. The method of claim 1, wherein the healthcare image is a Digital Imaging and Communications in Medicine (DICOM) image.

7. The method of claim 6, wherein the clinical report is not the interpretation of the DICOM image.

8. A graphical user interface embodied on at least one computer readable medium and executable by a computing device, for displaying a healthcare image for a patient and a clinical report simultaneously, the interface comprising:

a first display area configured to display a healthcare image for a patient; and a second display area configured to display a clinical report associated with a defined region of the healthcare image simultaneously with the healthcare image for the patient, wherein the clinical report is created based on results other than the healthcare image, and further wherein the defined region is a portion of the healthcare image.

9. The interface of claim 8, wherein the clinical report is a laboratory report.

10. The interface of claim 9, wherein the healthcare image is a radiology image.

11. The user interface of claim 10, wherein an accession number of a specimen collected for the patient for the laboratory report is associated with the radiology image for the patient.

12. A graphical user interface embodied on at least one computer readable medium and executable by a computing device, for displaying a radiology image for a patient and an associated laboratory image, the interface comprising:

a first display area configured to display a radiology image for a patient;

a second display area configured to display one or more graphical indicia each indicating a defined region of the radiology image, wherein the defined region is a portion of the radiology image;

a third display area configured to display a laboratory report associated with the defined region of the radiology image; and a fourth display area configured to display a laboratory image associated with the laboratory report.

13. The interface of claim 12, wherein the second display area is configured to display two graphical indicia each indicating a different defined region of the radiology image.

14. The interface of claim 12, wherein upon selection of the graphical indicia indicating a first defined region of the radiology image, the second display area is configured to display the laboratory report associated with the selected first defined region of the radiology image.

15. The interface of claim 12, wherein the second display area is visibly linked to the third and fourth display areas.

16. A graphical user interface embodied on at least one computer readable medium and executable by a computing device, for displaying a radiology image and a laboratory image associated with a patient, the interface comprising:
 a first display area configured to display a radiology image for a patient; and
 a second display area configured to display at least one laboratory image for the patient, the at least one laboratory image being associated with a defined region of the radiology image, wherein the defined region is a portion of the radiology image.

17. The user interface of claim 16, further comprising:
 a third display area configured to display a summary of a laboratory report for a patient the laboratory report being associated with the radiology image for the patient and the at least one laboratory image for the patient.

18. The user interface of claim 16, wherein the radiology image is a Digital Imaging and Communications in Medicine (DICOM) image.

19. The user interface of claim 18, wherein the at least one laboratory image is a non-DICOM image.

20. The user interface of claim 17, further comprising:
 a fourth display area configured to display a link to the complete laboratory report for the patient, the complete laboratory report for the patient being associated with the radiology image.

21. The user interface of claim 19, wherein the at least one laboratory image is a digital image of a pathology slide.

* * * * *